United States Patent [19]

Etienne et al.

[11] Patent Number: 4,966,150
[45] Date of Patent: Oct. 30, 1990

[54] ECHO TRACKING SYSTEM FOR APPARATUS FOR ULTRASONIC MEASUREMENT OF THE POSITION OF A MOBILE WALL

[75] Inventors: Jean-Daniel Etienne; Pierre-André Farine, both of Neuchâtel; Claude Bornoz, Fleurier, all of Switzerland

[73] Assignee: Asulab S.A., Bienne, Switzerland

[21] Appl. No.: 336,392

[22] Filed: Apr. 11, 1989

[30] Foreign Application Priority Data

Apr. 14, 1988 [FR] France .................................. 88 05065

[51] Int. Cl.⁵ .............................................. A61B 8/00
[52] U.S. Cl. .................... 128/661.04; 73/611
[58] Field of Search ...................... 128/661.04, 661.10, 128/661.05; 73/611

[56] References Cited

PUBLICATIONS

Emerson, R. et al., "Maximal Instantaneous Mitral Valve Velocities Measured With a Digital Echocardiographic Traching System", IEEE BME Trans., vol. BME-24, No. 1, pp. 71-73, Jan., 1977.
Hostetter, M. S. et al., "A Microprocessor-Controlled Echocardiographic Tracking System", IEEE BME Trans., vol. BME-27, No. 5, May, 1980.
Donnerstein, R. et al., "Digital Range-Gated Echocardiographic Tracking", Med. Instr., vol. 12, No. 3, May-Jun., 1978, pp. 184-188.
Groves, D. H. et al., "A Digital Technique for Tracking Moving Interfaces", UTS in Med. & Biology, vol. 8, No. 2, pp. 185-190, 1982.

*Primary Examiner*—Francis Jaworski
*Attorney, Agent, or Firm*—Sughrue, Mion, Zinn, Macpeak & Seas

[57] ABSTRACT

An echo tracker clamps a time window for detecting an echo at the position of an echo produced by a mobile wall receiving an ultrasonic pulse signal at a repetition rate $F_r$. It includes a depth counter (28) which counts in order to define the beginning of the time window in relation to a pulse of the pulse signal and which when it reaches a given value, supplies an enabling signal to activate authorization means (30) and a position detector (32).

Enabling means (30) provide an enabling signal for a given time which defines the detecting time window. During this time, the position detector counts until the echo is detected. The value reached at that instant is used to clamp again the time window and to modify the initial value of the depth indicator.

The invention is useful in the medical field for measuring the changes of the position of an interface between two tissues.

12 Claims, 5 Drawing Sheets

ECHO TRACKING SYSTEM FOR APPARATUS FOR ULTRASONIC MEASUREMENT OF THE POSITION OF A MOBILE WALL

BACKGROUND OF THE INVENTION

The instant invention relates to an echo tracking system for apparatus for measuring the position of a mobile wall.

The invention is useful in all fields where it is desired to follow the movement, over a period of time, of the position of a moving wall and in particular in the medical field. In the latter case, the invention may be employed to follow the changes over a period of time of the position of an interface between two tissues and as an example the depth of the anterior and posterior walls of a blood vessel to determine changes over a period of time in the diameter of this blood vessel.

Figure 1:
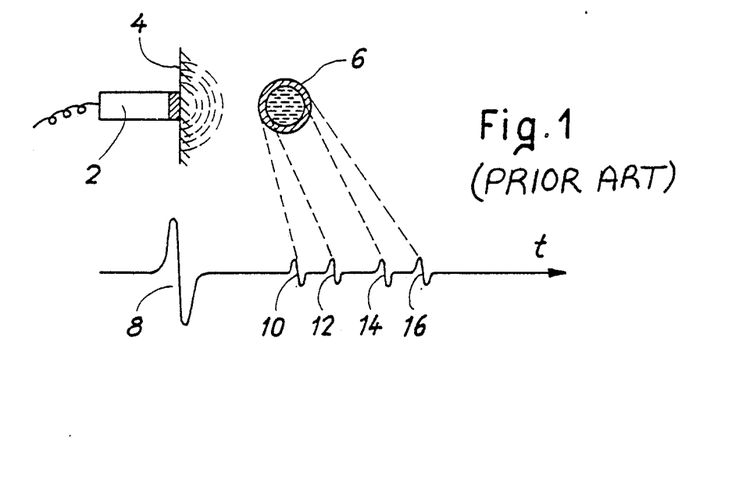
FIG. 1, already described, shows in diagrammatic form the principle of measurement of the position of a mobile wall.

FIG. 1 illustrates schematically the known principle of the measurement of the position of a mobile wall. This figure represents an ultrasonic wave transducer 2 placed on the skin 4 of a subject opposite a radial artery 6 shown in cross section. The transducer 2 is so controlled by an electronic circuit that it emits an ultrasonic wave pulse 8 and receives the echoes resulting from reflection of this pulse from the interfaces artery-tissue or artery-blood. Depending on the frequency of the ultrasound transducer, one can detect four distinct echoes 10, 12, 14, 16 or only two echoes corresponding to a combination of the echoes 10 and 12 and a to combination of the echoes 14 and 16 respectively.

The movement of an interface is determined in the following manner. The transducer 2 emits a pulse 8 with a repetition rate generally between 100 Hz and 20 kHz. In order to follow the position of the echo, whose delay after the pulse 8 depends on the position of the interface, a time window is used the width of which is fixed so as to define a time interval in which the echo is expected and which is opened with a delay which is adjustable after transmission of the pulse 8. This delay is adjusted after each cycle in a way so that the echo is detected in the center of this window if the interface is stationary.

Knowledge of the position of each interface as a function of time makes it possible, by noting the changes, to determine the changes in the diameter of the blood vessel 6 as a function of time.

Figure 2:
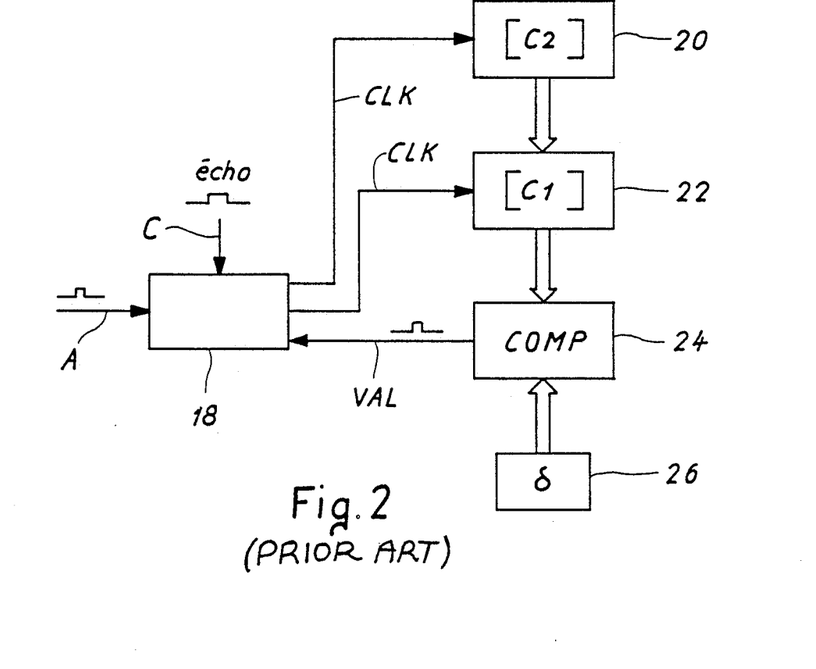
FIG. 2, already described, shows a prior art echo tracking system.

An echo tracking system is described in particular in the article "A phase-locked echo tracking system for recording arterial diameter changes in vivo" by D. E. Hokanson et al., published in the Journal of Applied Physiology, Vol. 32, No. 5, p. 728–733, 1972. This echo tracking system is essentially an analog system which limits its accuracy. More recently, digital echo tracking systems have been proposed. One such echo tracking system in particular is described in the article "A digital technique for tracking moving interfaces" by D. H. Groves et al., published in Ultrasound Med. & Biol., Vol. 8, No. 2, p. 185–190, 1982. FIG. 2 shows a circuit illustrating the structure of this digital echo tracking system and FIG. 3 shows a timing diagram illustrating the functioning of this circuit.

This echo tracking system comprises a logic circuit 18, a depth counter 20, an enabling counter 22, a digital comparator and a register 26. The logic circuit 18 receives a pulse signal A synchronous with the excitation signal applied to the transducer, a signal VAL delivered by the comparator 24 to indicate the beginning of the time window, and an ECHO signal which represents the echo received by the ultrasonic transducer after shaping and digitization. The logic circuit 18 includes a generator producing a clock signal CLK which is used to measure the echo delay over the pulse A and to clock the counters 20, 22.

Figure 3:
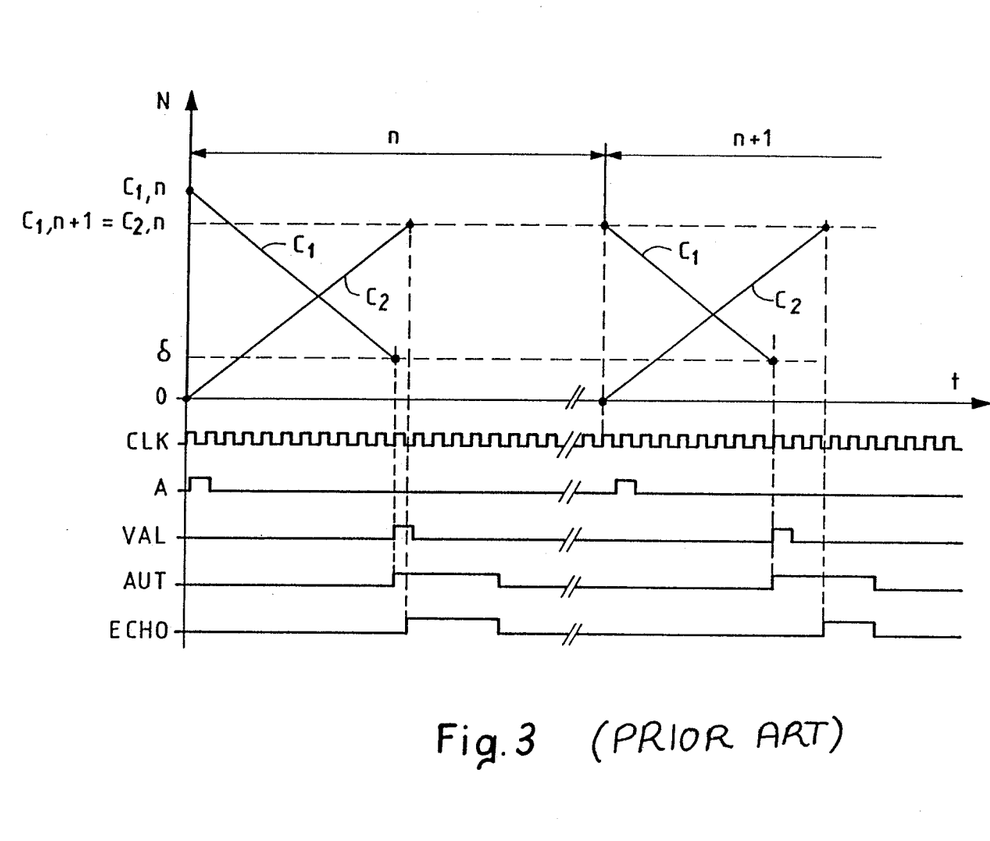
FIG. 3, already described, is a timing diagram illustrating the manner of operation of the echo tracking system of FIG. 2.

FIG. 3 illustrates the functioning of this echo tracking system for two consecutive cycles n and n+1. Shortly before the beginning of the cycle n, the counter 22 is stored with a value $C_{1,n}$ which, as will be seen below, is equal to the contents of the counter 20 at the end of the cycle n−1. This value is such that in counting down at the rate of the clock signal CLK the contents of the counter is equal to zero at the instant corresponding to the middle of the time window if the wall is stationary. At the moment when the time window has to be open the counter 22 thus has a value δ which is not equal to zero. To determine the beginning of the time window it is thus sufficient to compare the contents of the counter 22 to the fixed value δ. This is effected by the comparator 24 which receives on the one hand the value contained in the counter 22 and, on the other hand, the value δ memorized in the register 26.

As regards the counter 20, its content is set at zero shortly before the cycle n. Counting is stopped by the logic circuit 18 on reception of the echo C. The counter 20 then stores a value $C_{2,n}$ which represents the position of the mobile wall. This value is used in the following cycle n+1 to clamp again the position of the time window. This is effected in two stages: The content of the counter 20 is transferred into the counter 22, and the counter 20 is then reset.

It is known that echo tracking systems handle very high frequency digital signals. In the known echo tracking system shown in FIG. 2, the transducer transmits 3.5 MHz pulses at a repetition rate of 12.5 kHz and the clock signal CLK has a frequency of 20 MHz.

It follows that the echo tracking system shown in FIG. 2 has a high power consumption since the two counters 20, 22 and the comparator 24 are each in operation for a large part of each cycle. This is an obstacle against the production of a portable apparatus due to the considerable weight of the battery or accumulator needed if the power independency of the apparatus is to be reasonable.

It is moreover evident that there is a need for portable apparatus in fields such as the medical field. It would, indeed, be easier for a doctor to transport the apparatus from one room to another in a hospital to examine the patients rather than to have to move the patients to a fixed apparatus. A portable apparatus would also enable the doctor to examine a patient at home. Finally, a sufficiently small portable apparatus could be worn directly by the user, for example in the form of a wrist watch.

Another disadvantage of the known apparatus shown in FIG. 2 lies in its high cost which is in part due to the use of a very fast comparator. This is a bar to the industrial development of this type of apparatus.

SUMMARY OF THE INVENTION

It is an object of the invention to decrease the power consumption and to simplify the architecture of echo tracking systems in particular in order to produce at a reasonable price a portable apparatus for ultrasonic measurement of the position of a mobile wall.

The invention resides in a new construction of echo tracking system which involves a considerable reduction in power consumption and which makes it possible to eliminate the comparator.

More specifically, it is an object of the invention to provide an echo tracking system for ultrasonic measurement of the position of a mobile wall, comprising an input to receive a digital echo signal produced by reflection from said mobile wall of an interrogating ultrasonic pulse the transmission of which is controlled by a control pulse A transmitted at a repetition rate $F_r$, said echo tracking system comprising a clock delivering a clock signal CLK, enabling means delivering an enabling signal AUT to define the time window in which the echo is expected and a logic circuit to deliver a clamped again position signal POSREC of said window as a function of an echo position signal POSECH in the window, said echo tracking system further comprising:

a depth counter to define the beginning of said time window, said depth counter counting at the frequency of the clock signal CLK between said clamped again position signal and a first given value, the beginning of the counting being triggered by said control pulse and the depth counter supplying a validation signal VAL when it reaches said first given value to activate said enabling means, a position detector to determine the position of the echo in said time window, said position detector counting at the frequency of the clock signal CLK after a second given value, the beginning of counting being triggered by said validation signal and said position detector delivering to said logic circuit an echo position signal in said time window.

The clamped again position signal POSREC delivered by the logic circuit at the end of each cycle can be produced simply by effecting the algebraic sum of the POSREC signal stored at the beginning of the cycle in the depth counter and the POSECH signal delivered by the position detector.

The depth counter is preferably of the type having an output terminal delivering a signal having a first logic state when the content of the counter is different from zero and a second logic state when the content of the counter is equal to zero. In this case the value zero is chosen as the first given value and the signal taken at this terminal constitutes the validation signal.

According to another embodiment, the validation signal is supplied by the terminal delivering one bit of given weight of the binary data contained in the counter.

The enabling means may advantageously be a counter or a shift register and the enabling signal may be taken at a terminal of the enabling means in the same way as the validation signal is taken at a terminal of the depth counter.

It should be noted that the counters used in the invention serve to measure time intervals and that, for this reason, counting can be in either direction. The invention can therefore be executed both by up-counters and by down counters although, for simplicity's sake, only the term counter will be used in the text.

The characteristics and advantages of the invention may be seen from the following description, given as non limiting illustration with reference to the appended drawings, in which:

DETAILED DESCRIPTION OF THE PREFERRED EMBODIMENTS

Figure 4:
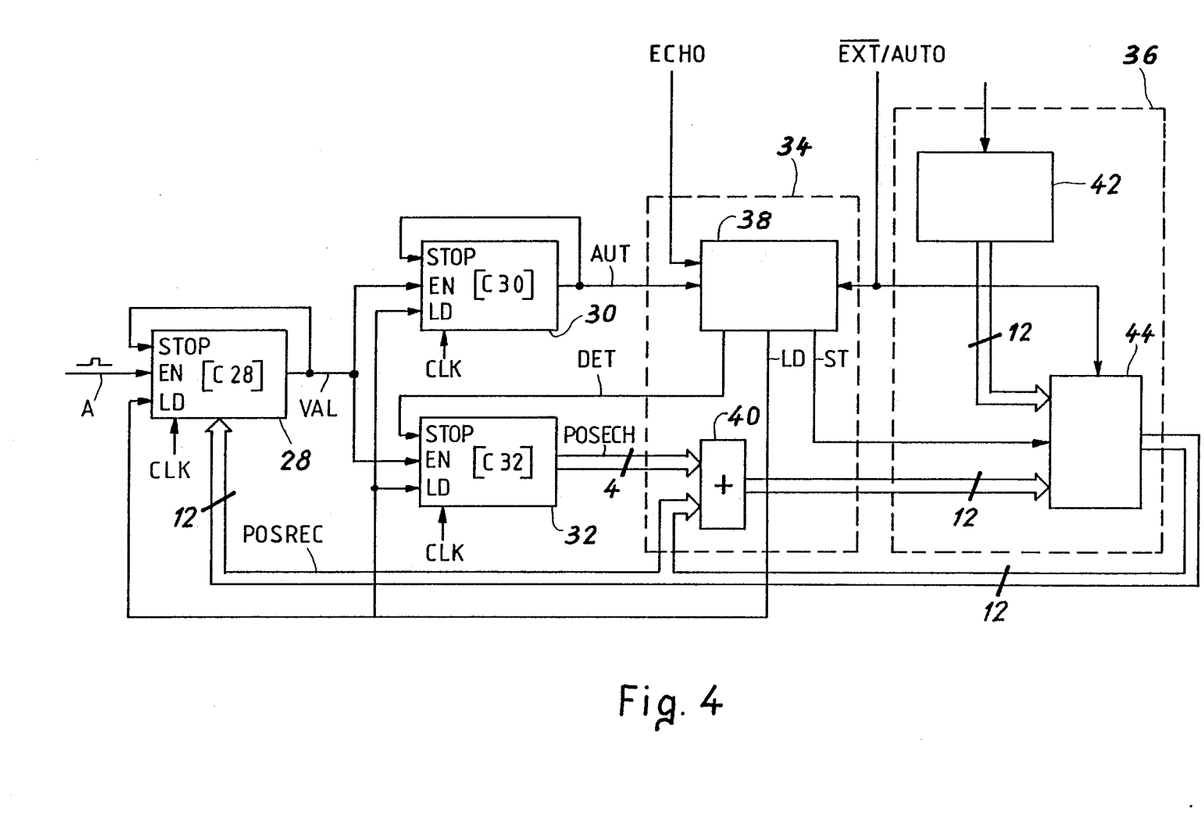
FIG. 4 illustrates an embodiment of an echo tracking system of the invention.

FIG. 4 shows an embodiment of the echo tracking system of the invention. This echo tracking system is intended to detect echoes corresponding to ultrasonic pulses transmitted with a repetition rate $F_r$ towards a mobile wall. For each echo the detection is enabled in a time window of given width, the position of which is linked to the moment of detection of the echo preceding the expected echo. For this purpose the echo tracking system comprises a depth counter 28 for determining the instant of opening of the time window, enabling means 30 for defining the width of the time window, a position detector 32 for memorizing the position of the echo received in the time window and a logic circuit 34 for clamping again the time window as a function of the position of the echo indicated by the position detector.

The echo tracking system shown in FIG. 4 also comprises an external control means 36 to modify the position of the time window independently of the position of the echo received. This means 36 is used in the setting up phase or, more generally, each time the echoes occur out of the window.

Figure 5:
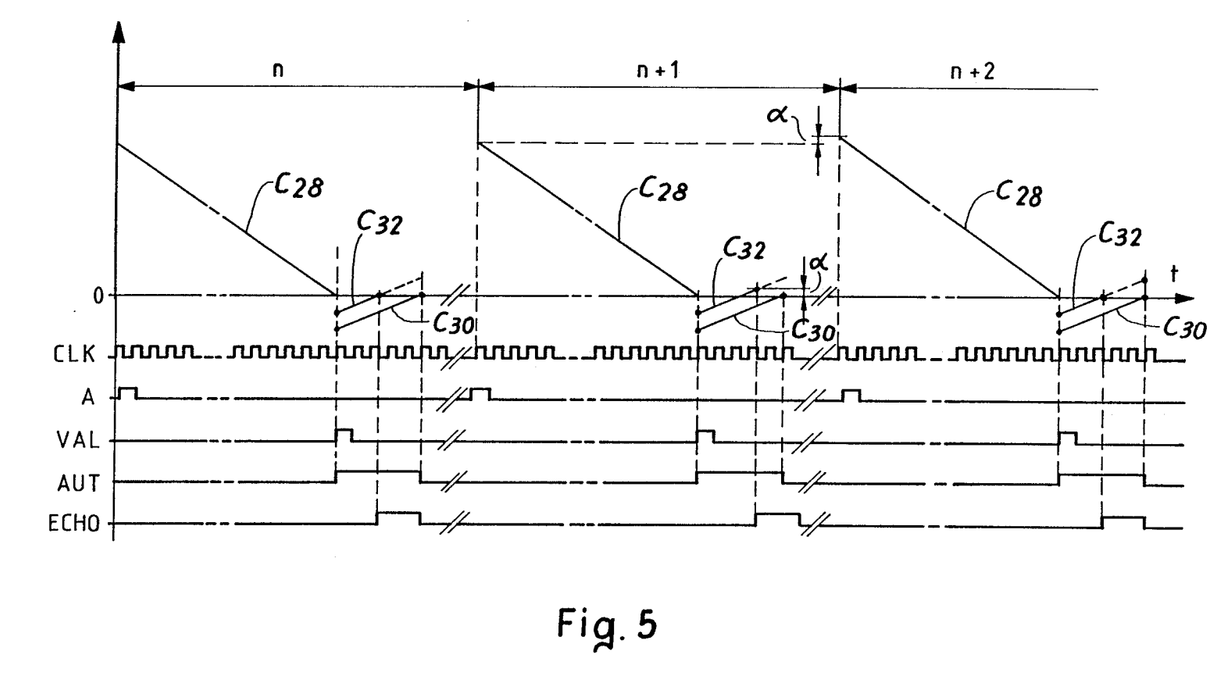
FIG. 5 is a timing diagram illustrating the functioning of the echo tracking system of FIG. 4.

The timing diagram of FIG. 5 illustrates the functioning of the echo tracking system. This executes successive cycles n, n+1, n+2... at the repetition rate $F_r$ of the control signal A. Before the beginning of each cycle the logic circuit 34 emits a signal LD to store given values into the depth counter 28, the enabling means 30 and the position detector 32.

The POSREC value stored in the depth counter 28 depends on the position of the echo in the window. This value is stored in a memory 44 which will be described below. The values stored in the enabling means 30 and the position detector 32 are fixed values contained in memories not shown in FIG. 4.

The value stored in the depth counter 28 is chosen in such a way that the counter delivers the validation signal VAL at the instant when the time window has to be opened. This validation signal is emitted when the counter contains a first given value. A depth counter is preferably used which is provided with an output terminal, the logic state of which is different according to whether the value contained in the counter is equal to zero or is different from zero. The validation signal is then obtained directly at this output terminal. The validation signal may also be composed in a simple manner by the value of one bit having a particular weight in the binary number contained in the counter. Indeed, it is sufficient to initially store the depth counter with a value chosen in such a way that the bit of the selected weight changes state at the instant at which it is desired to open the window.

The validation signal delivered by the depth counter 28 serves principally to activate the enabling means 30 and the position detector 32. It may also be applied to a STOP input of the depth counter 28 in order to stop the counting thereof.

On receipt of the validation signal the enabling means 30 delivers an enabling signal AUT of given length which defines the time window during which an echo is expected. This enabling means may be a counter. In this case the enabling signal may be produced in the same manner as the validation signal, that is it can be composed by the logic state of a bit of a given weight in the binary number contained in the counter or by the logic state of a bit having a different value depending on whether the content of the counter is equal to zero or is different from zero.

A different embodiment of the enabling means consists in using a shift register. In this embodiment the enabling signal may also be formed by the logic state of a bit of given weight of the shift register or by the value of a bit, the logic state of which is different depending on whether the content of the shift register is equal to zero or is different from zero.

For example, to produce an enabling signal at the high state for 5 periods of the clock signal CLK, it is possible to choose as enabling signal the value of the bit of the smaller weight of a shift register of 8 bits stored with the value "00011111". This bit has the value "1" during the 5 first shifts to the right controlled by the CLK signal and then passes to "0" as from the 6th shift to the right.

The position detector 32 is activated by the validation signal emitted by the depth counter 28. Its counting is stopped by a detection signal delivered by the unit 38 of the logic circuit 34 on an input STOP of the position detector 32 at the instant at which the echo signal occurs during the time window.

In this embodiment it is the logic unit 38 which detects the echo signal and which verifies that it appears in the time window. This verification can be simply effected by an AND logic gate. It is evident that one could also apply the echo signal directly onto the STOP input of the echo detector and then verify with the logic unit if the value contained in the position detector corresponds to an echo received inside or outside the time window.

The value POSECH contained in the position detector 32 shows the displacement to be applied to the window to recenter it on the echo received. This displacement is effected by an updating of the value stored by the logic circuit 34 into the depth counter 28. This updating is particularly simple if the initial value stored in the position detector 32 at the beginning of the cycle is chosen in such a way that, in the case of a stationary wall, the position detector has the value zero when the echo is detected. The value stored in the depth counter is then simply modified by adding thereto the value contained in the position detector 32. This is effected by an adding device 40. This stored value of the depth counter is memorized in a memory 44, access to which is authorized by a signal ST emitted by the logic unit 38.

The timing diagram of FIG. 5 illustrates the most important signal appearing on FIG. 4 as well as the values contained in the counters. The references C28, C30 and C32 correspond respectively to the content of the depth counter 28, of a counter forming the enabling means 30 and of the position detector 32.

Each measuring cycle starts with a control pulse of the signal A. This pulse initiates the counting of the counter 28 until the first determined value (equal to zero on FIG. 5) which generates the validation signal VAL.

This signal activates the enabling means 30 and the position detector 32. The enabling signal AUT, which defines the time window lasts for a predetermined period which, in FIG. 5, is equal to 5 periods of the CLK signal. This duration is defined the duration of a counting sequence up to a given value which is equal to zero in the figure.

As from the beginning of the time window, the position detector 32 changes its content until the appearance of the echo. The value at this instant is representative of the position of the echo in the window and thus the clamped again value of the position to be applied to the window.

On the figure the value stored in the position detector 32 is chosen so that, in the case of a stationary wall, the echo is detected when the position detector contains the value zero. This makes it possible to clamp again the window very easily, as shown by the successive cycles n, n+1, n+2.

During the cycle n, the echo appears in the center of the window (C32 is equal to zero). The window is thus in the correct position and the depth counter 28 is stored for the cycle n+1 with the same value as for the cycle n. The time window thus appears at the same instant in relation to the beginning of the cycle defined by the control pulse A, during the cycles n and n+1.

In cycle n+1 the echo appears in the window later on, showing that the mobile wall has moved away from the measuring apparatus. This delay is represented by a value $\alpha$ greater than zero in the position detector. To clamp the window again this value $\alpha$ is added to the value stored in the depth counter 28 for the cycle n+2.

If, on the other hand, the wall comes closer to the measuring apparatus, the echo appears before the middle of the window and the position detector then contains a negative value. It is also sufficient to add this negative value to recenter the window. One can of course replace the up-counter 32 by a down-counter and, in this case, the adding device is replaced by a subtracting device.

In FIG. 5 it will be noted that the signals A and CLK are independent. This is not necessary for the functioning of the echo tracking system, but makes it possible to effect a mean of the values of positions of the mobile wall. This results in an increase in the resolution as will emerge from the following description.

During normal functioning, the position of the window is automatically clamped again as a function of the position of the echoes. Nevertheless it is possible that the window may accidentally no longer be clamped on the echo signal, for example if the echo signal disappears for a certain time and that the mobile wall moves. In addition, when the apparatus is turned on, the echo does not necessarily appear in the window. For these reasons the echo tracking device shown in FIG. 4 is provided with an external control means for the position of the window.

This external control means 36 comprises a counter 42 and a memory 44 having two multiplexed inputs. The value contained in the counter 42 can be modified by an external up-counting or down-counting control signal. The value of the counter 42 is applied onto an input of the memory 44. The other input of this memory receives the value supplied by the adding device 40.

The selection between the manual mode and the automatic mode of clamping the window is defined by an external signal EXT/AUTO which selects on of the 5 inputs of the memory 44. This signal is also applied to the logic unit 38 which delivers the ST memory access signal 44.

By way of example, an echo tracking system corresponding to FIG. 4 and operating with a clock CLK of 60 MHz can comprise 12 bit counters of the type 74ACT191 for the depth counter 28, the enabling means 30, the position detector 32 and the counter 42, an adding device of the type 74HCT283 for the adding device 40 and an assembly comprising a memory of type 74HCT174 and a multiplexer of the type 74HCT604 for the memory 44. As regards the logic unit 38, it is possible to use an assembly of logic gates and bistable flip-flops well known to the person skilled in the art.

Figure 6:
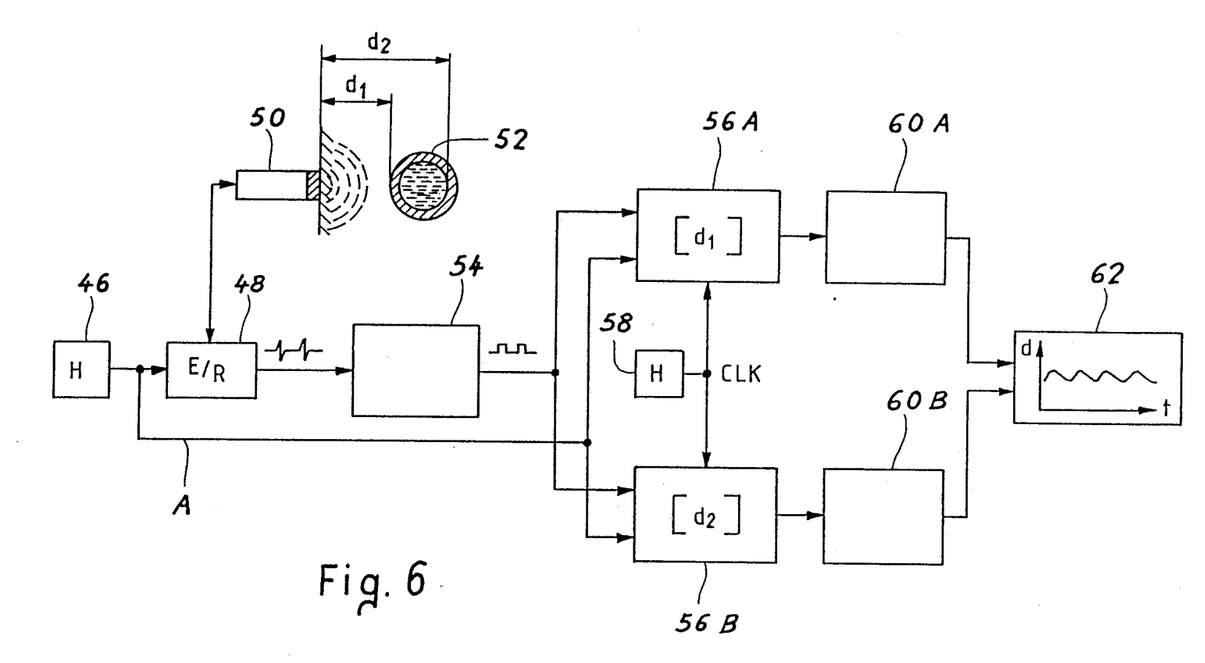
FIG. 6 shows an apparatus for measuring the position of a mobile wall including two echo tracking systems according to the invention.

The echo tracking system which has just been described is one element of an apparatus for the ultrasonic measurement of the position of a mobile wall. It has a structure which is simpler and less power-consuming than the known echo tracking system shown in FIG. 2. The echo tracking system of the invention may thus be integrated into a portable measuring apparatus. FIG. 6 shows a schematic representation of an embodiment of an apparatus of this type which is applied in the medical field for measuring the diameter of an artery.

This apparatus comprises a clock 46 delivering a pulse signal having a repetition rate of 5 kHz. This signal is received by a transmitter-receiver circuit 48 which controls an ultrasonic transducer 50. This transmits a pulse having a frequency of 10 MHz towards the artery 52 and receives the echoes reflected from the anterior and posterior walls of this artery. These echoes are delivered by the circuit 48 to a wave shaping means 54 comprising in known manner filtering means and an analog-digital converter.

The digital signal delivered by the wave shaping means 54 is applied to the inputs of two echo tracking systems 56A, 56B which each conform to the echo tracking system shown in FIG. 4. The echo tracking systems 56A, 56B, receive the same clock signal CLK of 60 MHz frequency delivered by a clock 58. In practice, each echo tracking system can also be implemented on an independent card comprising a clock CLK. In this case, each echo tracking system has its own clock. These clocks do not need to be synchronized.

The time windows of the echo tracking systems 56A and 56B are set respectively for the echo produced by the anterior wall and the echo produced by the posterior wall of the artery 52. Each echo tracking system thus delivers, at the repetition rate $F_r$, the position of the wall of the artery on which it is clamped, that is to say the distance between this wall and the transducer 50.

The sequence of the positions delivered by each echo tracking system is received in an averaging circuit 60A, 60B. Each circuit makes it possible, in known manner, to increase the accuracy of measurement by calculating the mean value of an assembly of values of consecutive positions or by making a sliding mean of a set of values of consecutive positions.

It is moreover known that the rough resolution $\epsilon_b$ of the position of a mobile wall is equal to $c/(2.F_{CLK})$, where c is the speed of sound in the medium situated between the transducer and the wall and $F_{CLK}$ is the frequency of the signal CLK when the effective resolution $\epsilon_e$ after averaging of the set of consecutive N positions is equal to $\epsilon_b/N$. This averaging operation is possible only if the clocks 46 and 58 are independent.

The values delivered by the averaging circuits 60A, 60B are received in a circuit 62 for evaluating the results. This circuit may comprise a memory unit and a display unit. It may also comprise a calculating unit for calculating the diameter of the artery 52 against time, by means of the difference in the positions of the anterior and posterior walls.

The circuit 62 may advantageously comprise a microcomputer. In this case the averaging may be easily be effected by means of software.

What is claimed is:

1. Echo tracking system for an apparatus for ultrasonic measurement of the position of a mobile wall, comprising an input to receive a digital echo signal produced by reflection from a mobile wall of an interrogating ultrasonic pulse the transmission of which is controlled by a control pulse (A) transmitted at a given repetition rate ($F_r$), said echo tracking system comprising:

clock means for delivering a clock signal (CLK);

enabling means for delivering, on reception of a validation signal (VAL), an enabling signal (AUT) which defines a time-window during which the echo signal is expected; and logic circuit means for receiving said digital echo signal and for delivering, at said repetition rate, a recenter position value (POSREC) which is a function of a received echo position value (POSECH) and which represents the time-position of the digital echo signal in said window; said echo tracking system further comprising:

depth counter means for counting at the frequency of said clock signal (CLK) between said recentered position value (POSREC) and a first given value, wherein the beginning of the counting is triggered by said control pulse (A), and said depth counter means emits said validation signal when it reaches said first given value; and position detector means for determining the position of the echo in said time-window, said position detector means counting at the frequency of the clock signal (CLK) from a second given value, wherein the beginning of counting is triggered by said validation signal, and said position detector means delivers said echo position value (POSECH) to said logic circuit means.

2. Echo tracking system according to claim 1, wherein said depth counter means comprises a terminal whose logic state is different depending on whether the content of said counter means is equal to or different from zero, and wherein said first given value is chosen as being equal to zero, and said validation signal is measured at said terminal.

3. Echo tracking system according to claim 1, wherein the validation signal is equal to the logic state of a bit of a given weight $r_1$ of the binary signal contained in said depth counter means, the recentered position value delivered by said logic circuit means being so calculated that said bit changes state at the instant when the window is to be opened.

4. Echo tracking system according to claim 1, wherein said enabling means (30) is a counter.

5. Echo tracking system according to claim 1, wherein said enabling means (30) is a shift register.

6. Echo tracking system according to claim 4 or 5, in which the enabling means comprises a terminal whose logic state is different depending on whether the content of the counter is equal to or different from zero, wherein said enabling signal is measured at said terminal.

7. Echo tracking system according to claim 4 or 5, wherein the enabling signal is equal to the logic state of a bit of given weight $r_2$ of the binary signal contained in the enabling means, said enabling means being loaded by said logic circuit means with a third given value so that said bit changes state at the moment when the window is to be closed.

8. Echo tracking system according to claim 1, wherein said position detector means is loaded by said logic circuit means with said second given value so that said position echo signal is equal to zero when the wall is stationary.

9. Echo tracking system according to claim 8, wherein said logic circuit means comprises means for delivering a recentered position value (POSREC) equal to the algebraic sum of the preceding recentered position value (POSREC) and the echo position value (POSECH) received from said position detector means.

10. Echo tracking system according to claim 1, further comprising external means (36) for displacing the time window, said external means delivering an adjustable recentered position value by an external control signal.

11. Echo tracking system according to claim 10, wherein said external means comprises a counter whose content constitutes said recentered position value, the external control signal acting on said counter to modify said recentered position value.

12. Echo tracking system according to claim 1, wherein the clock signal (CLK) and the control signal (A) are independent.

* * * * *